United States Patent [19]

Saito et al.

[11] 4,317,937
[45] Mar. 2, 1982

[54] PREPARATION AND USE OF BIS-(1-BROMO-2,3,3-TRICHLORO-2-PROPENYL) ETHER

[75] Inventors: Junichi Saito; Toyohiko Kume, both of Tokyo, Japan

[73] Assignee: Nihon Tokushu Noyaku Seizo K.K., Tokyo, Japan

[21] Appl. No.: 110,051

[22] Filed: Jan. 7, 1980

[30] Foreign Application Priority Data

Jan. 24, 1979 [JP] Japan .................. 54-6015

[51] Int. Cl.³ ........................... C07C 47/24
[52] U.S. Cl. .................................. 568/488
[58] Field of Search ........................ 568/488

[56] References Cited

U.S. PATENT DOCUMENTS 2,913,500 11/1959 Becke et al. ............... 568/681
3,980,755 9/1976 Black et al. ............... 568/488

FOREIGN PATENT DOCUMENTS 1285996 1/1969 Fed. Rep. of Germany ...... 568/488

OTHER PUBLICATIONS

Chemische Berichte, vol. 86, pp. 1469–1476, (1953).

Bukketin de la Societe Chimique France, pp. 1800–1806, (1959).

*Primary Examiner*—Werren B. Lone
*Attorney, Agent, or Firm*—Sprung, Felfe, Horn, Lynch & Kramer

[57] ABSTRACT

Bis-(1-bromo-2,3,3-trichloro-2-propenyl) ether of the formula

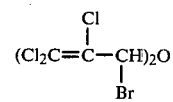

is produced by reacting bis-(2,3,3-trichloro-2-propenyl) ether of the formula

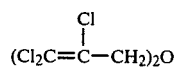

with bromine under irradiation with light. The end product as produced may be steam distilled in situ, thereby recovering 2,3,3-trichloroacrolein.

2 Claims, No Drawings

PREPARATION AND USE OF BIS-(1-BROMO-2,3,3-TRICHLORO-2-PROPENYL) ETHER

The present invention relates to the new compound bis-(1-bromo-2,3,3-trichloro-2-propenyl) ether, to a process for its preparation and to its use as an intermediate for producing trichloroacrolein.

The production of trichloroacrolein has been described in the literature, for instance (A) by hydrolysis of 1,1,2,3,3-pentachloropropylene, as disclosed in Chemische Berichte 86, 1469–1476 (1953), (B) by reaction of butyl vinyl ether, carbon tetrachloride and chlorine gas under appropriate reaction conditions, as disclosed in Bulletin de la Societe Chimique de France, 1800–1806 (1959), and (C) by oxidation of 2,3,3-trichloro-2-propenylalcohol, as described in West German Patent Specification No. 1,285,996.

Each of the above-listed known processes for producing trichloroacrolein has disadvantages which make the process unsuitable for production on an industrial scale.

The process (A) above uses a large amount of concentrated sulphuric acid in the reaction and the yield of the product is very low. Furthermore, the starting material, 1,1,2,3,3-pentachloropropylene itself is not readily available.

The process (B) involves complicated reaction sequences and requires very high temperatures, although the availability of starting materials and the yield of the product present no problems.

The process (C) has the drawbacks that the unreacted starting material, 2,3,3-trichloro-2-propenylalcohol, must be separated and that the starting material, 2,3,3-trichloro-2-propenylalcohol itself is not readily available.

There is therefore still a need for an industrially feasible and advantageous process for producing trichloroacrolein, which is useful as an intermediate for the preparation of certain dyestuffs, medicines and agricultural chemicals.

The present invention now provides, as a new compound, bis-(1-bromo-2,2,3-trichloro-2-propenyl) ether, which has the formula

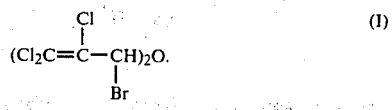
(I)

The present invention also provides a process for producing bis-(1-bromo-2,3,3-trichloro-2-propenyl) ether of the formula (I) above, characterized in that bis-(2,3,3-trichloro-2-propenyl) ether, of the formula

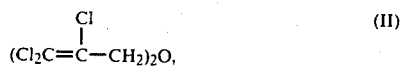
(II)

is reacted with bromine under irradiation with light, e.g. visible rays acting, mercury vapor, etc.

The invention also provides a process for producing trichloroacrolein, of the formula

(III)

which is characterized by steam distilling bis-(1-bromo-2,3,3-trichloro-2-propenyl) ether of the formula (I) above in the presence or absence of an inorganic acid.

In this process for producing trichloroacrolein, the intermediate (I) can be produced in situ. The process is then characterized by reacting bis-(2,3,3-trichloro-2-propenyl) ether of the formula (II) with bromine under irradiation with light to produce bis-(1-bromo-2,3,3-trichloro-2-propenyl) ether of the formula (I) above and then steam distilling the latter in the presence or absence of an inorganic acid.

The course of the bromination of bis-(2,3,3-trichloro-2-propenyl) ether is surprising, since one would expect the cleavage of the double bonds and the accompanying addition of bromine atoms. In fact, however, it has been found that, contrary to the expectation, the hydrogens on the 1-carbons of the ether are first attacked and substituted with bromine atoms with the double bonds left unreacted.

By means of the present invention, trichloroacrolein can be produced in a yield of 85–90% by a simple reaction process; furthermore, the novel compound produced is the intermediate stage of the reaction, bis-(1-bromo-2,3,3-trichloro-2-propenyl) ether of the formula (I), has a biological activity, especially a non-therapeutic bactericidal activity. The starting material for this novel compound, bis-(2,3,3-trichloro-2-propenyl) ether, is readily produced from trichloroethylene according to the process described in U.S. Pat. No. 2,913,500. Trichloroacrolein can be easily and advantageously produced, from the industrial point of view, in any of the cases: when trichloroethylene is used as a starting material, when bis-(2,3,3-trichloro-2-propenyl) ether is used as a starting material and when bis-(1-bromo-2,3,3-trichloro-2-propenyl) ether is used as a starting material. It is also possible to obtain trichloroacrolein in a good yield by successive reactions without isolating the novel compound bis-(1-bromo-2,3,3-trichloro-2-propenyl) ether of the formula (I) as the intermediate.

The present invention can be illustrated by the following reaction scheme:

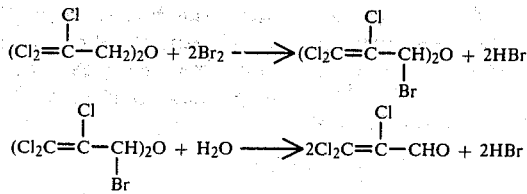

The production of bis-(1-bromo-2,3,3-trichloro-2-propenyl) ether is preferably carried out using a solvent or a diluent. Examples of suitable solvents and diluents are water and inert organic solvents such as aliphatic, alicyclic and aromatic hydrocarbons (which may optionally be chlorinated) such as hexane, cyclohexane, petroleum ether, ligroin, benzene, methylene chloride, chloroform, carbon tetrachloride, ethylene chloride, trichloroethylene and chlorobenzene.

The bromination reaction in the process of the present invention can be carried out over a wide range of temperature. Generally, it is carried out at a temperature from about −20° C. to the boiling point of the reaction mixture, preferably about 0° to 100° C. The reaction pressure is preferably normal pressure, although elevated or reduced pressure could be used.

Examples of the inorganic acids which may be used in the steam distillation of bis-(1-bromo-2,3,3-trichloro-2-propenyl) ether include hydrochloric acid, hydrobromic acid, nitric acid and sulphuric acid.

The present invention is illustrated in the following preparative examples:

EXAMPLE 1

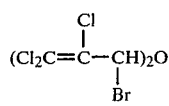

To a solution of 23.9 g of bis-(2,3,3-trichloro-2-propenyl) ether in 50 ml of chloroform was added dropwise a solution of 26.7 g of bromine and 20 ml of chloroform while irradiating with visible rays using two reflector lamps each having a capacity of 300 watts. The reaction temperature was maintained at the boiling point of chloroform and the addition rate was such that the color of bromine was slightly retained. After the addition, the refluxing was continued to complete the reaction. After the completion of the reaction, the chloroform solution was washed with 3% aqueous sodium bicarbonate solution and water successively and then dried over anhydrous sodium sulphate. The chloroform was distilled off and the resulting solid was recrystallized from n-hexane to give 28.8 g of the desired product, bis-(1-bromo-2,3,3-trichloro-2-propenyl) ether as colorless crystals; melting point 95°–96° C.

EXAMPLE 2

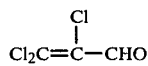

To 23.2 g of bis-(1-bromo-2,3,3-trichloro-2-propenyl) ether, as obtained in Example 1above, were added 100 ml of water and2 g of concentrated sulphuric acid and the resulting suspension was subjected to steam distillation. The end point of the steam distillation was detected by an aqueous hydrazine sulphate solution. The distillate was extracted with n-hexane, dried over anhydrous sodium sulphate and the n-hexane was distilled off to give 13.8 g of the desired product, trichloroacrolein; boiling point 101°–103° C./93 mm Hg.

EXAMPLE 3

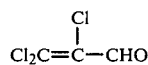

To a solution of 239 g of bis-(2,3,3-trichloro-2-propenyl) ether in 500 ml of chloroform was added dropwise a solution of 267 g of bromine and 200 ml of chloroform while irradiating with visible rays using two reflector lamps each having a capacity of 300 watts. The reaction temperature was maintained at the boiling point of chloroform and the addition rate was such that the color of bromine was slightly retained. After the addition, the irradiation with light and refluxing were continued to complete the reaction. After the completion of the reaction, the chloroform was distilled off under slightly reduced pressure and 1 liter of water and 20 g of concentrated sulphuric acid were added to the residue which was then subjected to steam distillation. The distillate was extracted with n-hexane, dried over anhydrous sodium sulphate and the n-hexane was distilled off to give 225 g of the desired product, trichloroacrolein; boiling point 101°–103° C./93 mm Hg.

EXAMPLE 4

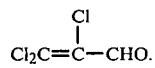

The procedures in Example 3 were repeated except that the scale was reduced to one-tenth. After the completion of the reaction, the chloroform was distilled off and the residue was subjected to steam distillation. The distillate was treated as in Example 2 to give 21 g of the desired product, trichloroacrolein; boiling point 101°–103° C./93 mm Hg.

It will be appreciated that the instant specification and examples are set forth by way of illustration and not limitation, and that various modifications and changes may be made without departing from the spirit and scope of the present invention.

What is claimed is:

1. In the production of trichloroacrolein of the formula

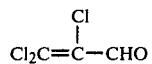

by reaction of a 2,3,3-trichloropropylene derivative, the improvement which comprises employing bis-(1-bromo-2,3,3-trichloro-2-propenyl) ether of the formula

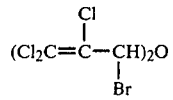

as such derivative, the reaction comprising steam distillation.

2. The process according to claim 1, wherein the steam distillation is effected in the presence of hydrochloric acid, hydrobromic acid, nitric acid or sulphuric acid.

* * * * *